United States Patent [19]

Dyer

[11] Patent Number: 4,620,531
[45] Date of Patent: Nov. 4, 1986

[54] BREEDING PHENOMENON

[76] Inventor: Jack L. Dyer, Rte. 3, Box 49, Los Lunas, N. Mex. 87031

[21] Appl. No.: 545,638

[22] Filed: Oct. 26, 1983

[51] Int. Cl.⁴ ............................................. A61F 5/00
[52] U.S. Cl. ..................................... 128/79; 604/349; 119/1
[58] Field of Search ............... 119/1; 604/349; 128/79

[56] References Cited

FOREIGN PATENT DOCUMENTS 0742099 11/1943 Fed. Rep. of Germany ...... 604/349
0067430 2/1944 Norway ............................... 604/349
0375066 3/1973 U.S.S.R. ............................... 604/349

OTHER PUBLICATIONS

*Breeding Management and Foal Development*, Equine Research, Inc., Tyler, Texas, 1982, pp. 335-341.
*Equine Stud Farm Medicine*, Rossdale, P. D., and S. W. Ricketts, 1980, pp. 140-141.
*Normal and Abnormal Sexual Behavior in the Equine Male*, Pickett, B. W., E. L. Squires and J. L. Voss, 1981, p. 25.

Primary Examiner—C. Fred Rosenbaum
Assistant Examiner—Gene B. Kartchner
Attorney, Agent, or Firm—Schmeiser, Morelle & Watts

[57] ABSTRACT

This invention is for method and apparatus for collecting seminal fluids from an animal and specifically for a breeding prototype with equipment and brackets which hold an artificial vagina in a position similar to the location of the vagina in a live female animal.

3 Claims, 6 Drawing Figures

U.S. Patent  Nov. 4, 1986  Sheet 1 of 4  4,620,531
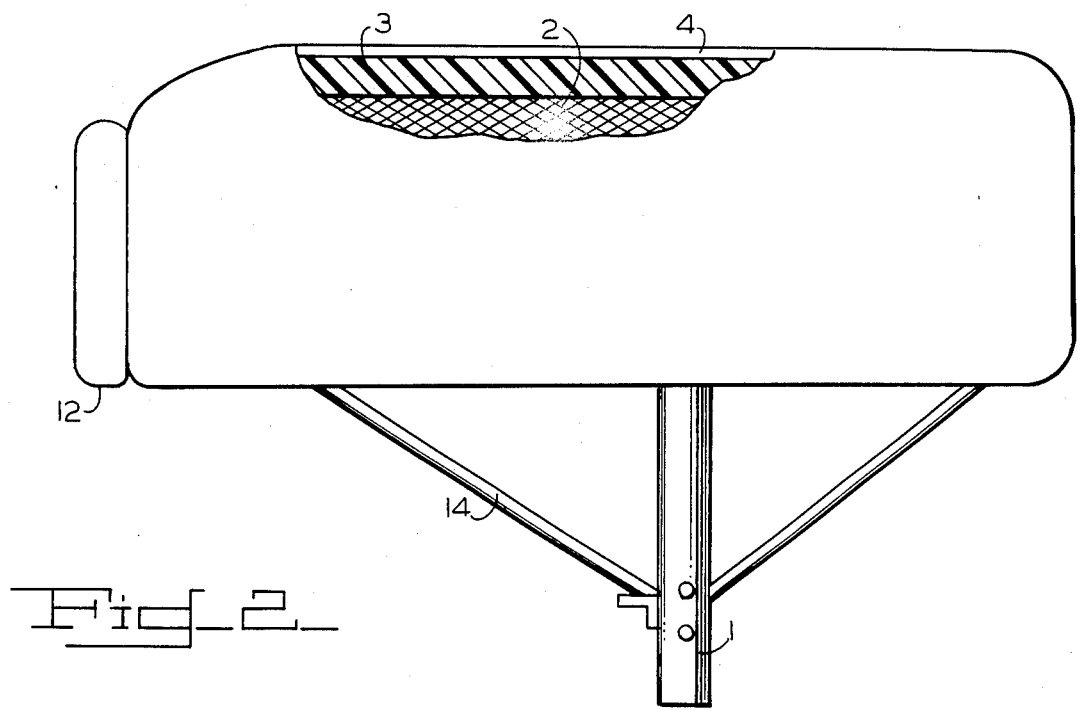
Fig_2_
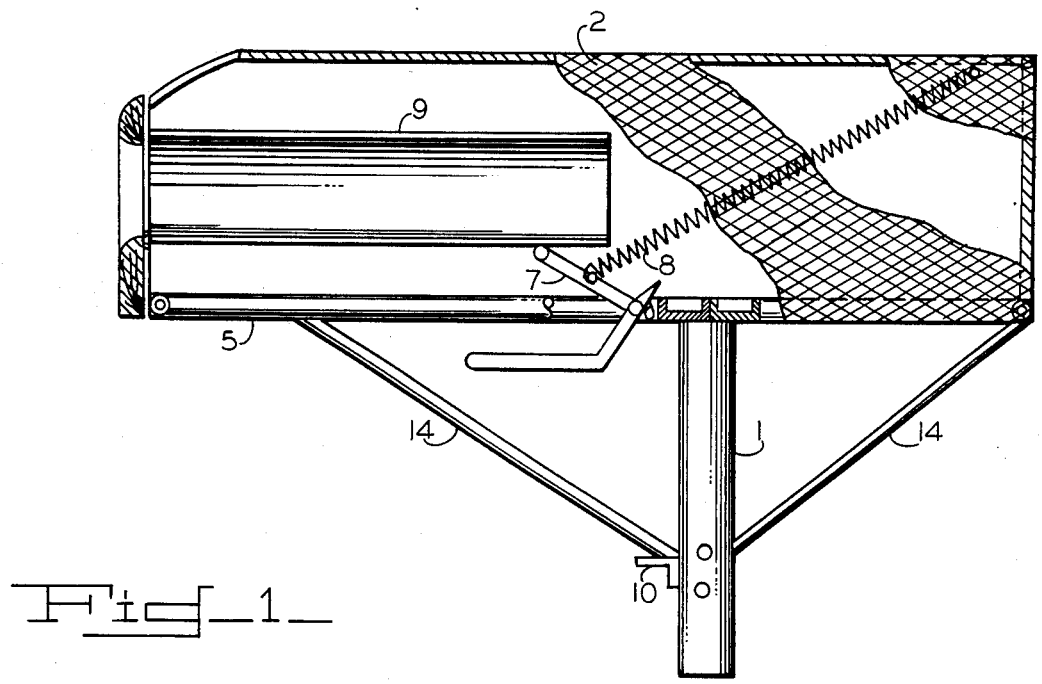
Fig_1_

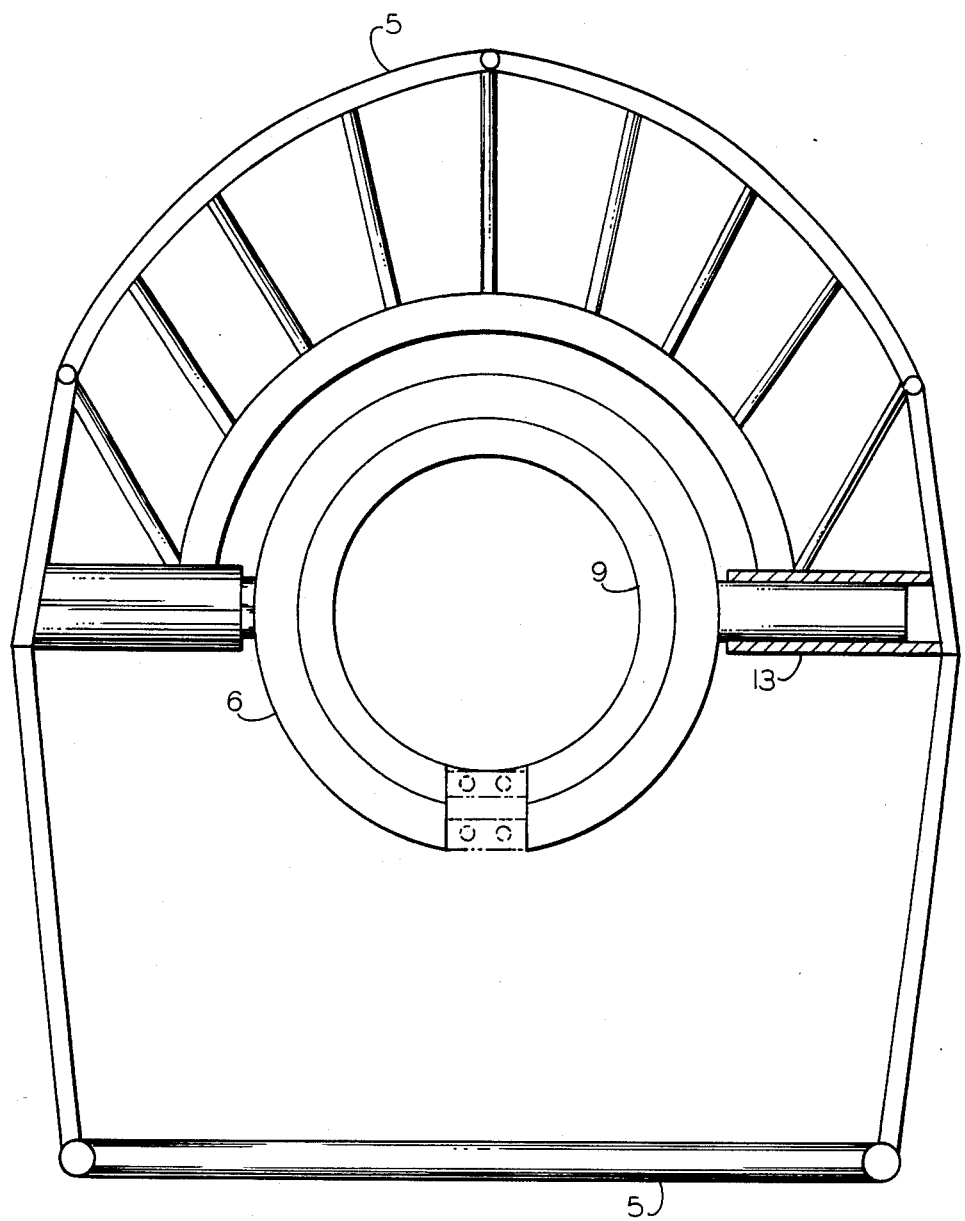

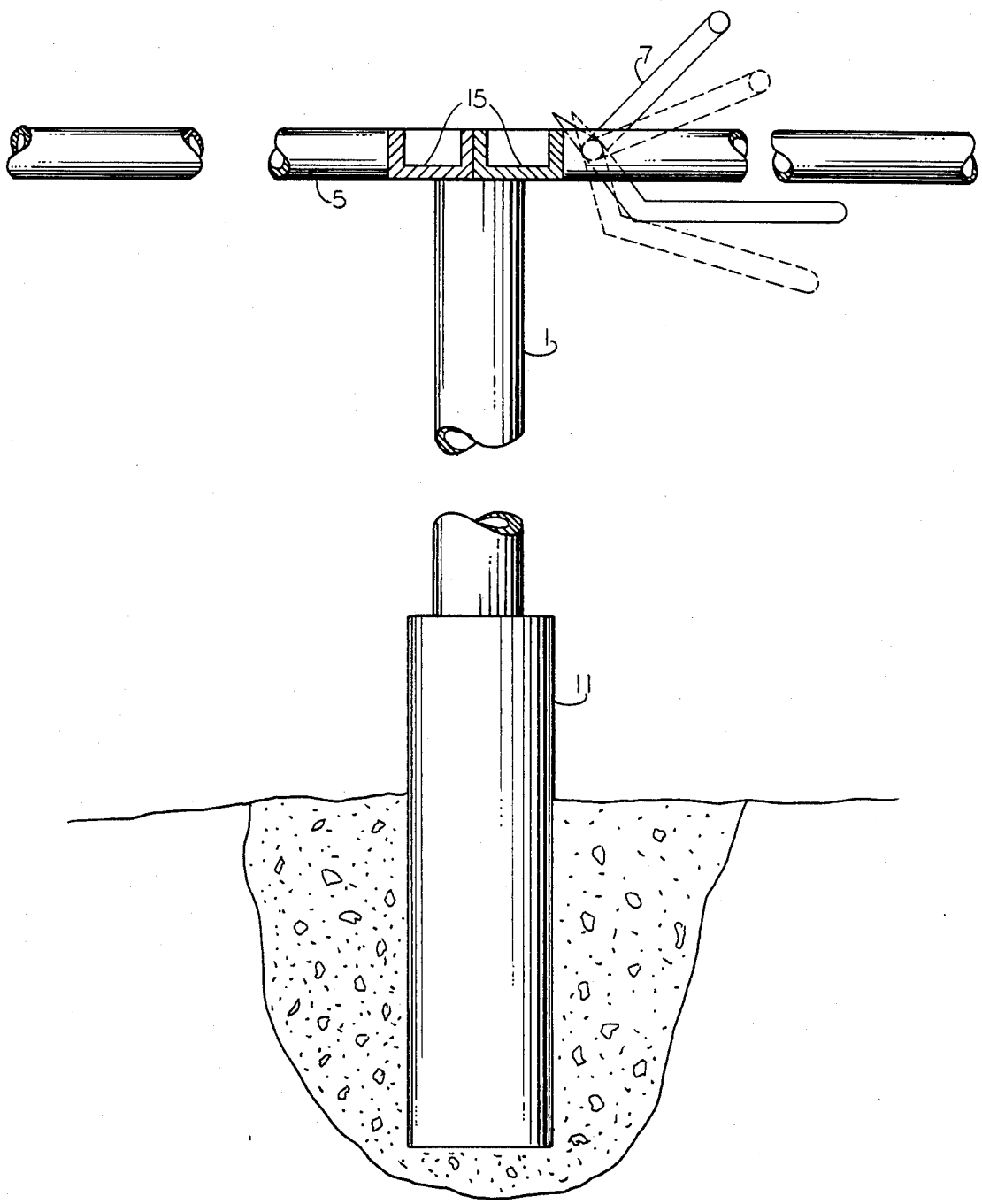
Fig_6_

BREEDING PHENOMENON

This invention relates to method and apparatus for obtaining semen from an animal for purposes of evaluation or artificial insemination. More specifically, it relates to an apparatus for holding an artificial vagina during the collection of semen from an animal.

It has become quite common to collect, or obtain, semen from animals and humans by means of an artificial vagina. The size, type, and structure of the artifical vaginas utilized in the collection of semen varies depending upon the subject whose semen is to be collected, the use of the semen, the facilities available, and the preference of the collector.

Artificial vaginas utilized to collect semen from animals must have certain properties, or characteristics. They must be rigid enough to withstand pressure, in some cases quite a lot, both internal and external during the process of collecting the semen; they must be of such size and weight to enable to the collector to hold and manipulate them, at times with one hand, they must maintain the internal temperature of 42 to 48 degrees centigrade for time sufficient to sexually arouse the animal and collect the semen; and they must have an inner liner which is soft and can be lubricated with a suitable lubricant (K-Y jelly or something similar) and still provide sufficient pressure to the penis of the animal to encourage behavior which leads to ejaculation.

Artificial vaginas in common use consist of some kind of tubular structure of the appropriate diameter and length, a rubber or rubber like liner which forms a water jacket on the inside of the tubular structure, and an inner liner of very soft rubber or latex material which is tapered on one end and leads to a container of some sort which is attached to the liner to receive the semen after ejaculation. Before collection, the water jacket is filled with water at the appropriate temperature and the inner liner is lubricated with a suitable lubricant. Artificial vaginas ready for use to collect semen from animals vary in weight from four or five pounds up to twenty-five pounds or more.

The prior art includes a number of devices which may be used to collect semen from a subject, human and animal, for example, and as presented in U.S. Pat. Nos. 3,421,504; 3,631,853; 3,910,262; 4,059,100; and 4,312,250. These and other artificial vaginas which are not patented may be used to collect semen from a subject, either human or animal. U.S. Pat. No. 4,312,350 depicts an artifical vagina especially designed for large animals. All of the artificial vaginas and/or devices depicted in the above must be prepared and held in place or operated by an attendant, or collector. As will be seen in the following presentation, holding an artificial vagina in hand while collecting semen from an animal has a number of distinct disadvantages. Henceforth, the discussion will be concerned with the collection of semen from animals only. The term "animal" as used herein is intended to include creatures such as stallions, bulls, boars, rams, and dogs, for example. However, it should be understood that it is not so limited.

Procedures for the actual collection of semen from an animal may vary; however, it is necessary for the animal to ejaculate deep in the artificial vagina. It is the usual practice to utilize another animal, preferably a female in season that with stand quietly, or an animal like artificial breeding dummy or phantom for the animal to mount prior to the actual collection of the semen. The animal from which the semen is to be collected must be aroused sexually in such a manner that he will attain and maintain an erection prior to and during the process of mounting and collection.

The method used to arouse the animal is very important. Some animals become so accustomed to the breeding area that they attain and maintain an erection upon entering the breeding area. Others must be stimulated in some way, some very carefully as they are so timid that they can be discouraged very easily. For these animals, it is customary to permit them to approach a receptive female, either directly or across a teasing board or chute of some sort. When the male animal attains and maintains an erection, it is customary to wash his penis with warm water and a mild cleansing agent. After thorough but gentle cleansing, the penis is carefully rinsed with warm, clear water.

When the artificial vagina has been properly prepared; filled with water of the desired temperature and adjusted for the animal, lubricated, and the animal has been washed and maintains his erection, he is permitted to mount the female or the breeding dummy. In the United States, stallions are approached both by the handler and the collector on the left side. However, in England, it is common practice for the handler and the collector to approach a stallion from the right side.

The actual techniques used in the collection of semen are very important as some animals are very sensitive. If improperly done, some animals may become uncooperative and fail to attain or maintain an erection. Others attain and maintain an erection but do not ejaculate in the artifical vagina.

When the animal actually mounts, the collector must act very quickly, efficiently, and carefully to insure that the penis of the animal is deflected into the artificial vagina. The collector must hold the artificial vagina with one hand and direct the penis of the animal into the artificial vagina with the other hand. The artificial vagina must be held in such a fashion and at such an angle that the thrusting animal realizes a sexually stimulating experience and ejaculates deep inside the artificial vagina.

Although the advantages of collecting semen from an animal in an artificial vagina are numerous, there are some technical and operational difficulties which must be overcome. Some animals are so aggressive when sexually aroused that they are difficult to control. Stallions and bulls present special problems of control as they are so large and powerful. Some become quite angry when sexually aroused and restrained and may strike out at their handler, another animal, or the collector. They can inflict severe damage, injury, and even death with their head/teeth and/or their feet. Fortunately, most animals respond to proper training and handling and learn that the entire process is rewarding. Others, however, especially stallions, may rear upon their back legs and charge the teaser animal or the breeding dummy.

On occasion, the teaser animal may become uncooperative and attempt to kick or move rapidly. Although hobbled and restained, she may still move so much that mounting or remaining mounted in the proper position becomes quite difficult for the male animal. At times, after successfully mounting the teaser animal, the animal being collected becomes so active that he becomes tangled in the restraining hobbles of the female. Also, some move around to the side of the teaser, in effect chasing the artificial vagina, so that it becomes difficult for the collector to hold the artificial vagina in the appropriate position. Some stallions make a concerted effort to savage, or bite severely, the teaser animal on the neck or shoulders. After the penis penetrates the artificial vagina, it is not uncommon for the penis and artificial vagina to form an angle of such a degree that it becomes painful to the animal being collected. Also, some animals may mount and penetrate the artificial vagina a number of times before ejaculating which means that the collector must monitor the temperature and lubrication of the artificial vagina and at times prepare it more than once.

Once the animal begins to ejaculate, he may relax so completely that he tends to fall away from the collector around the rear end of the teaser or the breeding dummy. Here again, this movement may create such an angle between the penis and the artificial vagina that the animal experiences pain and/or an incomplete ejaculation, or both. The artificial vagina must be maintained in a position hard against the hindquarter of the teaser animal, or against the back part of the breeding dummy. Therefore, another person or persons may be be required to be present opposite the collector to attempt to maintain the animal being collected in the proper position.

In addition, the collector must depend upon skilled and experienced assistants to control the animals during the process. Any one or all could suffer serious injury or death. The collector is placed in a position under the animal where injury is possible by being stepped on, kicked, or the animal dismounting without warning and coming down on the collector. Many farms, schools, and other breeding establishments require that hard hats and safety shoes be worn at all times. Also, it is quite possible for the animals to be injured in the process, especially when the animal to be collected mounts a teaser animal rather than a breeding dummy.

Any one or all of these problems, as well as others not included, may affect the animals or people, or both, so that a complete and satisfactory ejaculation does not occur. The prior art, especially the aforementioned U.S. Patents, appears to be concerned only with artificial vaginas and does not provide any means for overcoming the technical and operational problems associated with collecting semen from an animal, especially a large animal.

SUMMARY OF THE INVENTION

This invention is for method and apparatus for collecting seminal fluids and specifically for a breeding phenomenon, or phantom, with equipment and brackets which hold an artificial vagina in a position similar to the location of the vagina in a live female vagina. It consists of a framework of sufficient size and strength to accomodate the weight of the male animal from which semen is to be collected, steel mesh or any suitable material over the framework, padding of sufficient resiliency and thickness to absorb shock and prevent injury to the animal, a cover of suitable material, and a padded cover on one end with an opening large enough to accomodate an artificial vagina and the penis of the animal from which semen is to be collected.

The main object of the present invention is the provision of a device which is capable of improving the entire process of collecting semen from an animal when an artificial vagina is used. Another objective is to provide a device which is particularly adaptable for animals of any size.

The reasons for the collection of semen in an artificial vagina are many; however, in most cases the ultimate reason is for use in artificial insemination. Another objective of this invention is to improve the quantity and quality of the semen collected.

The welfare and safety of employees and animals necessary in semen collection is of utmost importance. At times, the process can be very hazardous. Another object of this invention is to eliminate safety hazards to both individuals and animals necessary in the process. Other objectives are to provide a device which is simple to use, is durable, contains a minimum of moving parts, and may be provided at a realistic cost.

It will be recognized that the foregoing is but one example of an apparatus and method within the scope of the present invention and that various other modifications will occur to those skilled in the art upon reading the disclosure set forth hereinbefore.

IN THE DRAWINGS

FIG. 1 is a pictorial representation partly in cross section of the breeding phenomenon of the present invention depicting the basic frame, supports, wooden cover for one end, covering over the basic frame, a receptacle for an artificial vagina, and a pivotal bracket and spring.

FIG. 2 is a pictorial representation of the exterior cover, the padding, padded cover for one end, and the basic support system.

FIG. 5 is a detailed representation depicting the pivotal collar mechanism for holding the receptacle for the artificial vagina.

FIG. 6 is a detailed representation of the support structure, the rotating bracket for supporting one end of the receptacle for the artificial vagina, and one method of installing the breeding phenomenon.

Figure 3:
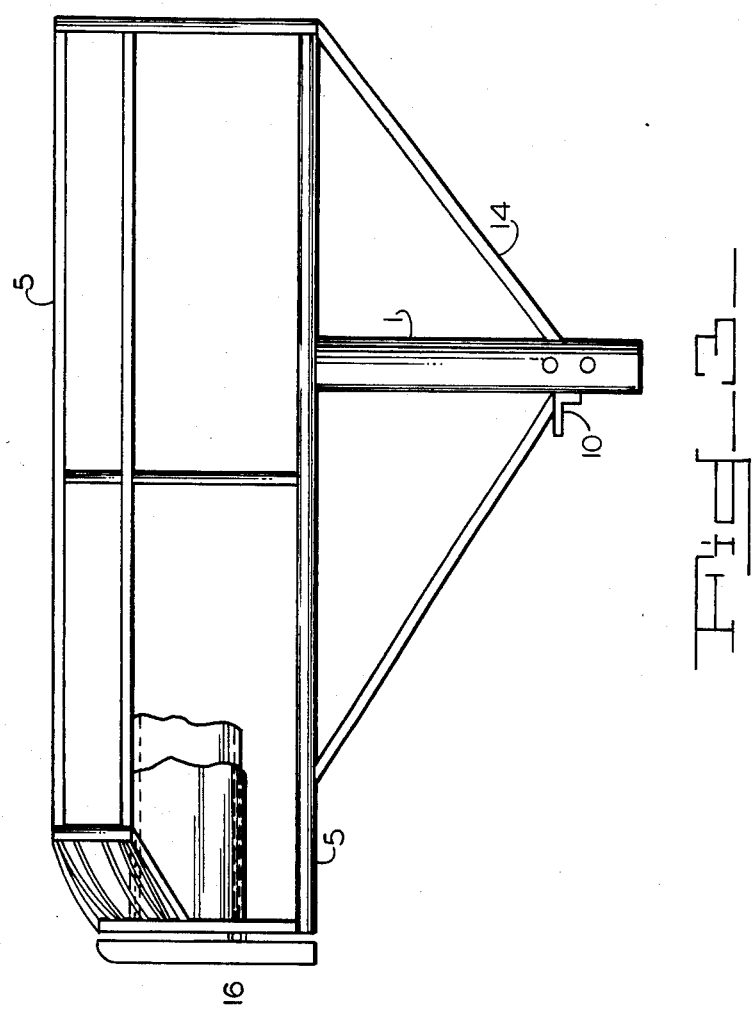
FIG. 3 is a pictoral representation of the basic frame, the hinged end piece, and the support system.
Figure 4:
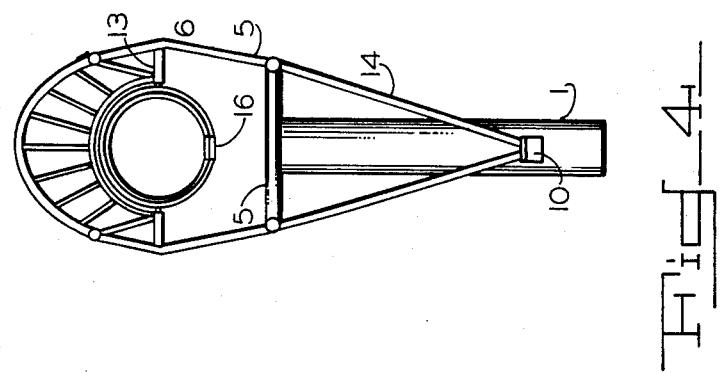
FIG. 4 is a pictorial representation of one end of the breeding phenomenon depicting the pivotal collar mechanism for holding the receptacle for the artificial vagina, and an end view of the receptacle for holding the artificial vagina.

In FIG. 1 there will be seen a frame (5) and supports (1) and (14) of sufficient size and strength to support the animal to be collected. The frame cover may be composed of steel mesh or any suitable material. A receptacle (9) of adequate diameter, length, and strength to accommodate the artificial vagina is attached to a rigid pivotal collar (6), FIG. 4, and rests on a pivotal bracket (7). A hinged or removable padded cover (12) FIG. 2, is shown with an opening, FIG. 1, through which the penis of the animal enters the artificial vagina. A spring (8) is attached to the frame (5) or the cover (2) and the pivotal bracket, (7).

As depicted in FIG. 1, the lower portion of the frame consists of supports (1) and braces (14) of sufficient size and strength to maintain stability of the breeding phenomenon when the animal mounts it. For convenience and ease of installation, the support (1) may be a pipe of sufficient size and length to support the breeding phenomenon. Another pipe (11), FIG. 6, may be embedded in concrete so that it extends above the base a length sufficient to support the breeding phenomenon.

Installation of the breeding phenomenon is accomplished by placing the pipe (1) either inside or outside the pipe (11) and adjusting the breeding phenomenon to the desired height. The height may be maintained by one or more bolts in holes in the pipes (1) and (11). Adjustments in height may be made by placing a jack under the bracket (10) and raising or lowering the breeding phenomenon to the desired height.

Use of the breeding phenomenon is rather simple and easy. Once the animal to be collected and the artificial vagina have been prepared as described earlier in this document, the artificial vagina is placed inside the receptacle (9). The animal is led to the near side and near the rear of the breeding phenomenon. He is encouraged to mount. At times it may be necessary to exercise control over some stallions as some tend to charge the breeding phenomenon from a distance. Once the animal begins to mount and rears upon his back legs, it may be necessary for the collector to guide the penis of the animal into the artificial vagina through the opening of the padded cover (12). With experience, most animals achieve penetration of the artificial vagina without assistance. Once penetration is achieved, the animal will thrust vigorously for a brief time and ejaculate deep in the artificial vagina.

When the animal begins to ejaculate, the pivotal bracket (7) is lowered. This permits the end of the receptacle (9) to drop to the lower position as the pivot collar (6) rotates. The semen is permitted to flow downward into the container which is attached to the artificial vagina.

After the animal begins ejaculating, the water valve on the artificial vagina may be opened to permit water to drain from the artificial vagina. This reduces the internal pressure in the artificial vagina and permits all of the semen to flow into the attached container. After the animal dismounts, the opening of the artificial vagina may be covered, more water drained from the artificial vagina, the pivot bracket (7) returned to the original position, and the artificial vagina removed and taken to the areas where the semen is to be processed and used or stored.

Use of the breeding phenomenon eliminates many of the difficulties associated with the collection of semen from an animal into an artificial vagina. It increases the quantity and quality of the semen ejaculated, is much more satisfactory for the animal, and eliminates most of the safety hazards of the collection process. In addition, with a trained animal, it is possible for one person, rather than two or more to complete the entire process.

What is claimed is:

1. An apparatus for securing therein an artificial vagina at a position equivalent to the location of the vagina in a live animal comprising:
   a padded animal phantom of suitable size and material having therein means for securing and operating an artificial vaginal mechanism, said means further comprising:
   a rigid collar means pivotally mounted at the rear of said phantom;
   an open-ended tubular receptacle, rigidly attached at one end of said collar means, said receptacle proper being enclosed within the body of said phantom;
   movable lever support means allowing the enclosed end of said receptacle to be repeatedly raised or lowered during collection as said collar means rotates on its pivotal mount so as to allow the tilting of an artificial vagina mechanism which has been secured therein.

2. The invention of claim 1 further comprising a padded door piece having an opening therethrough to allow penetration of the penis while further securing said artificial vaginal mechanism.

3. The invention of claim 2 wherein said opening is an annular converging orifice which directs the penis into said artificial vaginal mechanism and allows collection deep within it.

* * * * *